(12) United States Patent
Lee et al.

(10) Patent No.: US 12,009,099 B2
(45) Date of Patent: Jun. 11, 2024

(54) DISEASE DIAGNOSIS SYSTEM FOR SUPPORTING DUAL CLASS, AND METHOD THEREFOR

(71) Applicant: DEEP BIO INC., Seoul (KR)

(72) Inventors: Sanghun Lee, Seoul (KR); JoonYoung Cho, Seoul (KR); Sun Woo Kim, Seongnam-si (KR)

(73) Assignee: DEEP BIO INC., Seoul (KR)

( * ) Notice: Subject to any disclaimer, the term of this patent is extended or adjusted under 35 U.S.C. 154(b) by 844 days.

(21) Appl. No.: 16/972,231

(22) PCT Filed: Jun. 4, 2019

(86) PCT No.: PCT/KR2019/006758
§ 371 (c)(1),
(2) Date: Dec. 4, 2020

(87) PCT Pub. No.: WO2019/235827
PCT Pub. Date: Dec. 12, 2019

(65) Prior Publication Data
US 2021/0142900 A1    May 13, 2021

(30) Foreign Application Priority Data
Jun. 4, 2018 (KR) .......................... 10-2018-0064331

(51) Int. Cl.
*G16H 50/20* (2018.01)
(52) U.S. Cl.
CPC ................................. *G16H 50/20* (2018.01)
(58) Field of Classification Search
None
See application file for complete search history.

(56) References Cited

U.S. PATENT DOCUMENTS 7,467,119 B2    12/2008    Saidi et al.
9,514,416 B2    12/2016    Lee et al.
(Continued)

FOREIGN PATENT DOCUMENTS

KR    10-2014-0042531    4/2014
KR    10-2016-0034814    3/2016
(Continued)

OTHER PUBLICATIONS

L.-C. Chen, G. Papandreou, I. Kokkinos, K. Murphy and A. L. Yuille, "DeepLab: Semantic Image Segmentation with Deep Convolutional Nets, Atrous Convolution, and Fully Connected CRFs," in IEEE Transactions on Pattern Analysis and Machine Intelligence, vol. 40, No. 4, pp. 834-848, Apr. 1, 2018. (Year: 2018).*
(Continued)

*Primary Examiner* — Robert A Sorey
(74) *Attorney, Agent, or Firm* — PnK IP LLC

(57) ABSTRACT

A disease diagnosis system includes a processor and a storage device storing a neural network. The processor trains the neural network in the storage device to output a determination value corresponding to a probability having at least one of a plurality of states using a given loss function and learning data labeled so that a given unitary unit included in a biometric image is to have at least one of the plurality of states. The neural network includes a specific layer to output a plurality of feature values corresponding to a probability that the unitary unit is to be determined as each of the plurality of states. The loss function incorporates both first and second feature values corresponding to first and second states into a dual labeling unitary unit with the first state having a higher probability and a second state having lower probability.

8 Claims, 5 Drawing Sheets

(56) References Cited

U.S. PATENT DOCUMENTS

| | | | |
|---|---|---|---|
| 9,858,389 B2* | 1/2018 | Donovan | G16H 50/50 |
| 10,417,525 B2 | 9/2019 | Ji et al. | |
| 2004/0199482 A1* | 10/2004 | Wilson | G16H 50/20 |
| | | | 706/924 |
| 2014/0101080 A1 | 4/2014 | Lee et al. | |
| 2015/0213302 A1 | 7/2015 | Madabhushi et al. | |
| 2016/0086078 A1 | 3/2016 | Ji et al. | |
| 2017/0068887 A1 | 3/2017 | Kwon | |
| 2017/0200266 A1* | 7/2017 | Podilchuk | G06T 7/0012 |
| 2018/0240233 A1* | 8/2018 | Kiraly | G06T 7/0012 |
| 2019/0005686 A1* | 1/2019 | Liu | G16H 30/40 |
| 2019/0065897 A1* | 2/2019 | Li | G06F 18/2415 |
| 2019/0073569 A1* | 3/2019 | Ben-Ari | G16H 50/70 |
| 2019/0197358 A1* | 6/2019 | Madani | G06N 3/045 |
| 2019/0197368 A1* | 6/2019 | Madani | G16H 30/40 |
| 2019/0198156 A1* | 6/2019 | Madani | G06N 3/082 |
| 2019/0205758 A1* | 7/2019 | Zhu | G06T 7/13 |
| 2019/0244076 A1* | 8/2019 | Madi | G06N 3/08 |
| 2019/0385306 A1 | 12/2019 | Kim | |
| 2019/0392253 A1 | 12/2019 | Ji et al. | |
| 2020/0020097 A1* | 1/2020 | Do | G06F 18/2413 |

FOREIGN PATENT DOCUMENTS

| | | |
|---|---|---|
| KR | 10-2016-0037022 | 4/2016 |
| KR | 10-2018-0021635 | 3/2018 |
| KR | 10-2018-0066983 | 6/2018 |

OTHER PUBLICATIONS

International Search Report dated Oct. 4, 2019, issued in International Application No. PCT/KR2019/006758 (with English Translation).

Lecture Notes of 'Joint Detection and Diagnosis of Prostate Cancer in Multi-parametric MRI Based on Multimodal Convolutional Neural Networks' from MICCAI 2017 dated Sep. 4, 2017.

'Semantic segmentation for prostate cancer grading by convolutional neural networks' from Proceedings of SPIE dated Jun. 21, 2018.

* cited by examiner

DISEASE DIAGNOSIS SYSTEM FOR SUPPORTING DUAL CLASS, AND METHOD THEREFOR

CROSS-REFERENCE TO RELATED APPLICATION

This application is a National Stage Entry of International Application No. PCT/KR2019/006758, filed on Jun. 4, 2019, and claims priority from and the benefit of Korean Patent Application No. 10-2018-0064331, filed on Jun. 4, 2018, each of which is hereby incorporated by reference for all purposes as if fully set forth herein.

BACKGROUND

Field

The present invention relates to a disease diagnosis system using a neural network and a method thereof and, more particularly, to a system that may train a neural network to diagnose a disease, allows labeling for a specific unitary unit (e.g., pixels of an image corresponding to a biometric tissue) in a dual class, and may construct the neural network having higher accuracy, and a method thereof.

Discussion of the Background

One of the important tasks performed in pathology or a pathology department is to perform diagnosis for determining a state or symptom of a specific disease by reading a biometric image of a patient. Such diagnosis is a method dependent on the experiences and knowledge of a long experienced healthcare worker.

With the recent development of machine learning, attempts to automate a task of recognizing or classifying an image using a computer system are actively made. In particular, attempts to automate diagnosis, performed by an experienced healthcare worker, using a neural network (e.g., a deep learning method using a convolutional neural network (CNN)), that is, a kind of machine learning, are sought.

In particular, in diagnosis through deep learning using a neural network (e.g., CNN), a feature of a disease factor not known to an experienced healthcare worker is found out in that experiences and knowledge of an experienced healthcare worker are not simply automated as in a prior art, but a desired answer is derived by autonomously finding feature elements through learning.

In general, the diagnosis of a disease through a neural network using a biometric image uses a piece, that is, a patch (or also called a tile) of a biometric image. That is, an experienced healthcare worker annotates a state of a specific disease (e.g., whether cancer has been revealed) with respect to a corresponding patch, and trains the neural network using a plurality of such annotated patches as training data. In this case, a CNN may be used as the neural network.

However, such a method has a problem when part within a corresponding patch is a disease that cannot be known because the neural network is trained to determine whether a disease is revealed for each patch (e.g., 512 by 512 pixels).

Furthermore, in a conventional unit, the neural network is trained to determine only one disease state (e.g., whether a disease is present or not present or which state if a disease is present (e.g., a Gleason score value in the case of prostate cancer)) for each unitary unit (e.g., patch), that is, an input unit of the neural network. However, if an experienced healthcare worker determines each unitary unit, there is a possibility that the unitary unit may have a first state and may have a second state. That is, it is not evident that the unitary unit has any one of a plurality of states, but there may be a good possibility that the unitary unit has the first state, but there is a possibility that the unitary unit may have the second state.

In such a case, conventionally, there is a possibility that a specific unitary unit may have a given state of a plurality of states. However, such a possibility is neglected. Assuming that the specific unitary unit has any one specific state, learning data is generated through labeling, and a neural network trained using such learning data treats, as a unitary unit having a clear and specific state, a unitary unit having a possibility that the unitary unit may have a plurality of states.

However, in such a case, if the information itself that has a possibility that a specific unitary unit may have a plurality of states is incorporated into learning as meaningful information, the information itself may become meaningful information, and may improve the accuracy of a neural network.

The above information disclosed in this Background section is only for understanding of the background of the inventive concepts, and, therefore, it may contain information that does not constitute prior art.

SUMMARY

Exemplary embodiments provide a system, which can achieve improved performance by allowing characteristic features of a unitary unit, having possibilities of a plurality of states, to be used for training if input data (unitary unit) is not clearly classified as any one of classes output by a neural network, such as a first state or a second state, but the unitary unit has the possibilities of the plurality of states because a determination of a class to be classified is ambiguous, and a method thereof.

Furthermore, exemplary embodiments provide a system supporting a deep learning model capable of fine segmentation for a portion where a disease is revealed and a portion where a disease is not revealed by performing diagnosis for each pixel not diagnosis for each patch, and a method thereof.

A disease diagnosis system includes a processor and a storage device storing a neural network and using a biometric image and the neural network. The processor is configured to train the neural network and stored in the storage device, to output a determination value corresponding to a probability having at least one of a plurality of states using a given loss function and learning data labeled so that a given unitary unit included in the biometric image is to have at least one of the plurality of states. The neural network includes a specific layer to output a plurality of feature values corresponding to a probability that the unitary unit is to be determined as each of the plurality of states. The loss function is defined to calculate a loss by incorporating both a first feature value corresponding to a first state and a second feature value corresponding to a second state, among feature values of the specific layer, into a dual labeling unitary unit labeled to have the plurality of states, including the first state determined to have a state of a higher probability and a second state determined to be lower than the first state, among multiple unitary units.

The loss function may be defined so that the second feature value has more losses than the first feature value.

The loss function may be defined as Equation 1 below.

$$L(x) = -\log \frac{e^{x_{primary}} + p \cdot e^{x_{secondary}}}{\sum e^{x_i}} \quad \text{[Equation 1]}$$

wherein i may indicate the plurality of states, $\chi_i$ may be a feature value corresponding to an i-th state among the plurality of states, $\chi_{primary}$ may be the first feature value, and $\chi_{secondary}$ may be the second feature value.

The unitary unit may be a pixel unit of the biometric image.

If each pixel has a preset determination value, the processor may determine a corresponding pixel as a disease pixel corresponding to a disease based on a determination value of the pixel unit, and may indicate the disease pixel differently from another pixel in the biometric image based on a result of the determination.

The disease may be prostate cancer.

The plurality of states may include a normal, a Gleason score 3, a Gleason score 4, and a Gleason score 5.

A method implemented in a system including a processor and a storage device and performed by a disease diagnosis system using a biometric image and a neural network includes the steps of receiving, by the neural network stored in the storage device, a given loss function and learning data labeled so that a given unitary unit included in the biometric image is to have at least one of a plurality of states, and training to output a determination value corresponding to a probability having at least one of the plurality of states using the received learning data with respect to each unitary unit. The neural network includes a specific layer to output a plurality of feature values corresponding to a probability that the unitary unit is to be determined as each of the plurality of states. The loss function may be defined to calculate a loss by incorporating both a first feature value corresponding to a first state and a second feature value corresponding to a second state, among feature values of the specific layer, into a dual labeling unitary unit labeled to have the plurality of states, including the first state determined to have a state of a higher probability and a second state determined to be lower than the first state, among multiple unitary units.

The method may further include the steps of determining a corresponding pixel as a disease pixel corresponding to a disease based on a determination value of the pixel unit if each pixel has a preset determination value, and indicating the disease pixel differently from another pixel in the biometric image based on a result of the determination.

The method may be implemented through a computer program installed on a data processor and hardware of the data processor capable of executing the computer program.

There is an effect in that improved performance can be achieved because characteristic features of a unitary unit having possibilities of a plurality of states are used for training if input data (unitary unit) is not clearly classified as any one of a plurality of states, but the unitary unit has the possibilities of the plurality of states because a determination of a class is ambiguous upon labeling.

Furthermore, there is an effect in that fine segmentation for a portion where a disease is revealed and a portion where a disease is not revealed is possible by performing diagnosis for each pixel not diagnosis for each patch.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
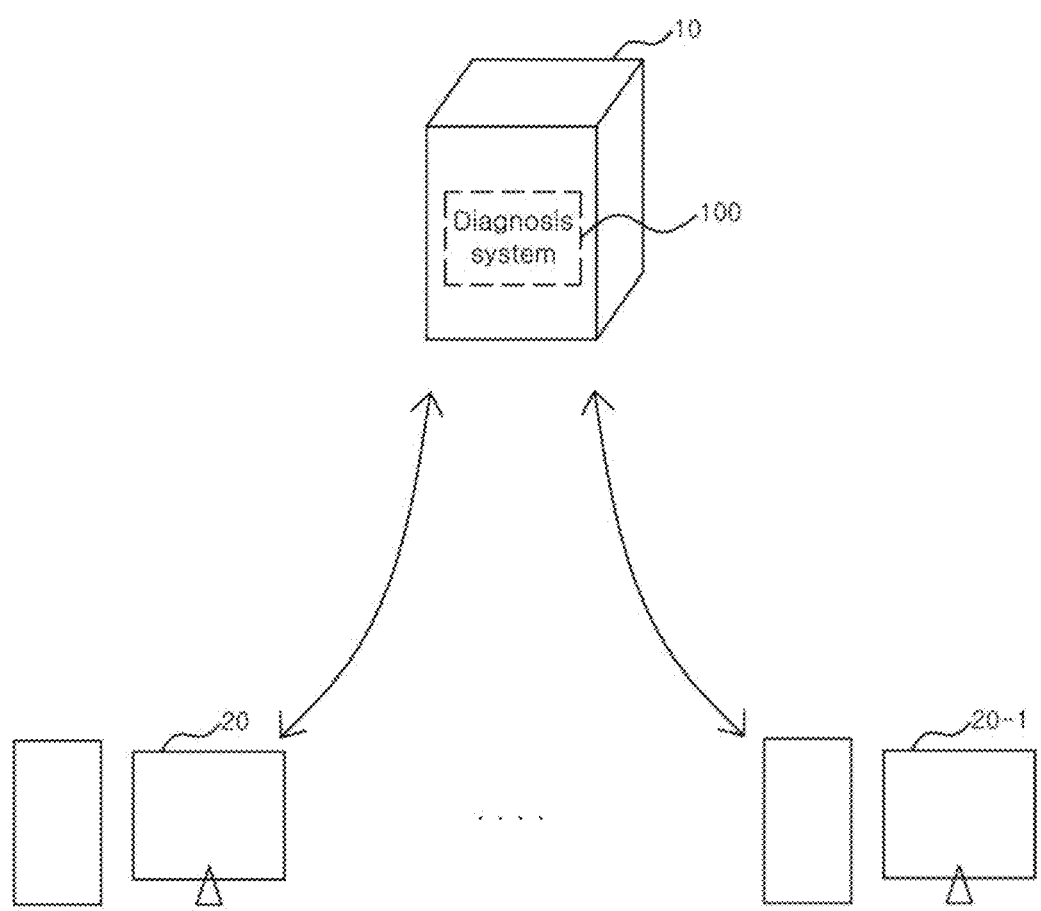
FIG. 1 is a diagram illustrating a schematic system configuration of a disease diagnosis system using a neural network according to an exemplary embodiment.

As customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

The invention may be modified in various ways and may have various exemplary embodiments. Specific exemplary embodiments are to be illustrated in the drawings and are to be described in the detailed description in detail. It is, however, to be understood that the invention is not intended to be limited to the specific exemplary embodiments, but that the invention includes all of modifications, equivalents and/or substitutions which fall within the technological scope of the invention. In describing the invention, a detailed description of the known technologies will be omitted if it is deemed to make the gist of the invention unnecessarily vague.

Terms, such as a first and a second, may be used to describe various elements, but the elements should not be restricted by the terms. The terms are used to only distinguish one element from the other element.

The terms used in this application are used to merely describe specific exemplary embodiments and are not intended to restrict the invention. An expression of the singular number includes an expression of the plural number unless clearly defined otherwise in the context.

In this specification, a term, such as "include or "have", is intended to designate that a characteristic, a number, a step, an operation, an element, or a part described in the specification, or a combination of them exists, and should be understood that it does not exclude the existence or possible addition of one or more other characteristics, numbers, steps, operations, elements, parts, or combinations of them in advance.

Furthermore, in this specification, if one element "transmits" data to the other element, this means that one element may directly transmit the data to the other element or may transmit the data to the other element through at least another element. In contrast, if one element "directly transmits" data to the other element, this means that the data is transmitted from one element to the other element without the intervention of another element.

Hereinafter, the invention is described in detail based on the exemplary embodiments of the invention with reference to the accompanying drawings. The same reference numerals proposed in the drawings denote the same member.

FIG. 1 is a diagram illustrating a schematic system configuration of a disease diagnosis system using a neural network according to the exemplary embodiments.

Referring to FIG. 1, the disease diagnosis system using a neural network (hereinafter the diagnosis system 100) according to the exemplary embodiments is installed in a given server 10, and may implement the exemplary embodiments. The server 10 means a data processing unit having the operation ability for implementing the exemplary embodiments. In general, an average expert in the technical field of the exemplary embodiments may easily infer that not only a data processing unit accessible to a client over a network, but any device capable of performing a specific service, such as a personal computer or a mobile terminal, may be defined as the server.

Figure 3:
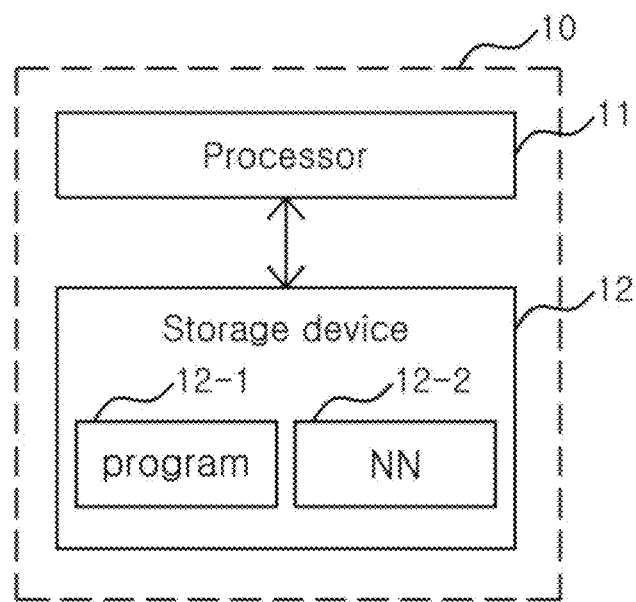
FIG. 3 is a diagram for describing a hardware configuration of the disease diagnosis system using a neural network according to an exemplary embodiment.

As illustrated in FIG. 3, the server 10 may include a processor 11 and a storage device 12. The processor 11 may mean an operation device capable of driving a program 12-1 for implementing the exemplary embodiments. The processor 11 may perform diagnosis using the program 12-1 and a neural network 12-2 defined by the exemplary embodiments.

The program 12-1 may mean software defined to implement the exemplary embodiments.

The storage device 12 may mean data storage means capable of storing the program 12-1 and the neural network 12-2, and may be implemented as a plurality of pieces of storage means according to an implementation example. Furthermore, the storage device 12 may be meant to include not only a main storage device included in the server 10, but a temporary storage device, a memory, etc. which may be included in the processor 11.

The diagnosis system 100 has been illustrated as being implemented as any one physical device in FIG. 1 or 3, but an average expert in the technical field of the exemplary embodiments may easily infer that a plurality of physical device may be organically coupled to implement the diagnosis system 100 according to the exemplary embodiments, if preferable.

Hereinafter, in this specification, when it is said that the diagnosis system 100 performs a given function, this may mean that the processor 11 can perform the given function using the program 12-1.

In this specification, when it is said that the diagnosis system 100 performs diagnosis, this may mean a series of processes of receiving a biometric image in which a biometric tissue is represented for each given unitary unit and outputting output data defined in this specification.

The unitary unit may mean a unit in which diagnosis is performed. According to an example, the unitary unit may be a pixel unit of a biometric image. According to embodiments, the unitary unit may be a patch unit of a biometric image, and may be a slide unit.

In this specification, if the unitary unit is a pixel unit, accordingly, a case where a result diagnosed for each pixel by the diagnosis system 100 will be determined to be a pixel in which a disease has been revealed or a pixel in which a disease has not been revealed is described as an example. However, according to an implementation example, an average expert in the technical field of the exemplary embodiments may easily infer that the unitary unit may be different.

The output data may mean information output by the output layer of a neural network used by the diagnosis system 100. The output data may include state information indicating that a biometric tissue corresponding to a unitary unit included in a biometric image is any state for a specific disease.

For example, the state information may be information corresponding to the probability that a specific disease (e.g., a specific type of cancer) has been revealed in a tissue corresponding to a unitary unit. Alternatively, as will be described later, the state information may be information (or the probability that the state information will correspond to a progression of a specific disease) indicative of the degree of progress in addition to whether a specific disease is revealed simply. For example, as will be described later, if the exemplary embodiments is used for the diagnosis of prostate cancer, a Gleason pattern or a Gleason score, that is, an index indicative of a progression of prostate cancer, may be included in the state information. For example, the Gleason pattern has values of 2 to 5, and indicates that a degree that prostate cancer has been revealed is severe as the value becomes greater. Accordingly, the state information may include information corresponding to the probability that a biometric tissue corresponding to a unitary unit, that is, a target for diagnosis, will correspond to a specific value (e.g., 3, 4, or 5) of the Gleason pattern or information corresponding to the probability that the biometric tissue will correspond to a "normal" (i.e., if a disease has not been revealed).

The state information may be present in plural. For example, according to the exemplary embodiments, a state may be implemented as four channels. For example, a first state may be a state in which a corresponding unitary unit will be a normal, a second state may be a state in which a Gleason pattern is 3, a third state may be a state in which a Gleason pattern is 4, and a fourth state may be a state in which a Gleason pattern is 5.

A feature value corresponding to each state channel may be a value corresponding to the probability of each state. The neural network may be trained so that the possibility is increased as the value is increased.

A layer that outputs such feature values corresponding to a plurality of states may be the final layer of the neural network, and may be a layer right before the final layer. In the case of the latter, the previous layer that outputs feature values corresponding to a plurality of states may output feature values corresponding to a plurality of states (e.g., the aforementioned four states). The final layer may output, as an output value, a state (e.g., any one of the normal, and the Gleason patterns 3, 4, and 5) having the greatest value of feature values of a previous layer.

Alternatively, the final layer may be a layer that outputs the plurality of states. This may be easily changed according to embodiments in which a neural network is designed.

According to the exemplary embodiments, learning data of the neural network is not labeled as any one of the plurality of states, but may be labeled as the plurality of state.

That is, an experienced healthcare worker or an expert who can label which state a unitary unit has by checking the unitary unit by the naked eye may not clearly check which one of the plurality of states the unitary unit has, but there may be a possibility that the unitary unit will be classified as the first state or the second state.

That is, there is a possibility that a unitary unit of a biometric image used as learning data is not clearly classified as any one state, but the unitary unit may have the plurality of states, that is, the unitary unit has an ambiguous state.

In such a case, conventionally, although the unitary unit has ambiguity, any one of the plurality of states is selected. The corresponding unitary unit is labeled as the selected state. The neural network is trained based on such a labeling result.

However, according to the exemplary embodiments, an image characteristic itself having ambiguity may have useful information. Such an image characteristic is not predicted as any one class (state) having a good possibility, but the image characteristic having ambiguity is labeled as it is. In this case, the neural network may be trained to have higher accuracy compared to a conventional method.

For example, an expert who performs labeling may determine that there is a good possibility that a given specific unitary unit will be classified as the first state (e.g., normal), but there is a small possibility that the specific unitary unit will be determined as the second state (e.g., the Gleason score 3).

Such a case and a unitary unit which may be clearly classified as the first state (e.g., normal) may correspond to a case where there is any fine difference in an image characteristic. However, if a unitary unit is simply labeled as any one state (e.g., normal) that appears to have a high probability according to a conventional method, this may result in a result in which the fine difference is neglected.

However, according to the exemplary embodiments, a unitary unit having such ambiguity is labeled as it is (i.e., the first state determined to have a higher probability and a state which has a lower probability than the first state, but may be the second state), but may be labeled to be different compared to a case where the unitary unit is labeled as any one of the first state or the second state. Furthermore, according to such a method, that is, a method of labeling a unitary unit as a plurality of states (in this specification, a case where the unitary unit is labeled as two states is illustrated, and thus called "dual class labeling"), performance of the neural network can be improved because a specific unitary unit itself labeled in a dual class is incorporated into learning.

In the case of such a dual class labeling method, a loss function capable of incorporating features of dual class labeling needs to be defined.

For example, a specific unitary unit may be labeled as a primary state, that is, a state determined to have a high probability, and a secondary state. That is, a unitary unit having an ambiguous (confusable) image characteristic may be labeled in a dual class as described above.

In such a case, the loss function to define the neural network may be defined to incorporate both the primary state and the secondary state. For example, if the neural network outputs the primary state with a high probability, the neural network is defined to have a high compensation (low loss). If the neural network outputs the secondary state with a high probability, the neural network is defined to have a low compensation (high loss). In this case, the loss function may be defined to be reduced only when a feature value of the secondary state is output with a high probability compared to another state not the primary state or the secondary state.

Accordingly, since the neural network is trained to reduce a loss as much as possible, the neutral network is trained to output the primary state as the state of unitary unit labeled in a dual class with a high probability, also may be trained to have feature values corresponding to a high probability as the state of unitary unit compared to another state although the secondary state has a lower probability than the primary state.

Accordingly, in the case of a unitary unit having a confusable image characteristic, a confusable state itself is incorporated into learning. Accordingly, there is an effect in that a diagnosis system based on deep learning and having higher accuracy can be constructed because a confusable image characteristic is not neglected, but is also incorporated into diagnosis results of the neural network.

Meanwhile, if the diagnosis system 100 is included and implemented in the given server 10, the diagnosis system 100 may perform communication with at least one client (e.g., 20, 20-1) capable of accessing the server 10. In such a case, the client (e.g., 20, 20-1) may transmit a biometric image to the diagnosis system 100. The diagnosis system 100 may perform diagnosis according to the exemplary embodiments on the received biometric image. Furthermore, the diagnosis system 100 may transmit diagnosis results to the client (e.g., 20, 20-1).

The diagnosis system 100 may perform diagnosis using the neural network according to the exemplary embodiments. In order to perform such diagnosis, the diagnosis system 100 may first perform a process of training the neural network using learning data labeled as any one of a plurality of state channels or in a dual class.

Accordingly, the diagnosis system 100 may be a system for performing diagnosis using the neural network trained according to the exemplary embodiments and a program that performs diagnosis using the neural network and that is received from the outside, and may be a system for performing even the training of the neural network. Furthermore, the diagnosis system 100 is not a general-purpose data processor, but may be implemented as a dedicated device fabricated to implement the exemplary embodiments. In such a case, the diagnosis system 100 may further include means for scanning a biometric image.

The neural network may be a network for receiving information (e.g., red-green-blue (RGB) 3-channel information) of a given unitary unit (e.g., pixel or patch) and outputting, as feature values, a plurality of pieces of state information of the corresponding unitary unit for a given disease (e.g., prostate cancer), respectively, or outputting any one state having the highest probability among the plurality of pieces of state information.

According to an example, the neural network uses a known Resnet neural network, and may be a method using a DeepLab model.

According to another exemplary embodiment, the neural network may be a neural network using both a micronetwork and a macronetwork, as disclosed in a Korean Patent Application (a Korean Patent Application No. 10-2016-0168176, System and method for medical diagnosis using neural network, hereinafter referred to as "the prior application") filed by the present applicant.

In such a case, the micronetwork may receive a unitary unit. The macronetwork may receive a surrounding unitary unit including the unitary unit, and may output state information related to the unitary unit. For example, if the unitary unit is a pixel unit, the micronetwork may be defined to receive a specific pixel, and the macronetwork may be defined to receive given input data including even surrounding pixels of the specific pixel and to output a state of the specific pixel. In such a case, learning having higher accuracy may be possible because not only one unitary unit, but even a surrounding unitary unit may affect a determination of whether a disease is revealed in a corresponding unitary unit. Furthermore, there is an effect in that accuracy can be improved to a very meaningful level with respect to the diagnosis of a disease in which even a state of a tissue around a biometric tissue actually corresponding to a specific unitary unit must be considered in addition to the biometric tissue in order to diagnose the biometric tissue depending on a disease. Furthermore, if a biometric image is segmented into multiple unitary units, there is an effect that is robust against the influence of diagnosis results, which may occur depending on a method of segmenting a patch or that a segmented region corresponds to which location of a biometric tissue.

Contents disclosed in the prior application may be included as a reference for the exemplary embodiments. In this specification, a detailed description of contents disclosed in the prior application is omitted.

Figure 2:
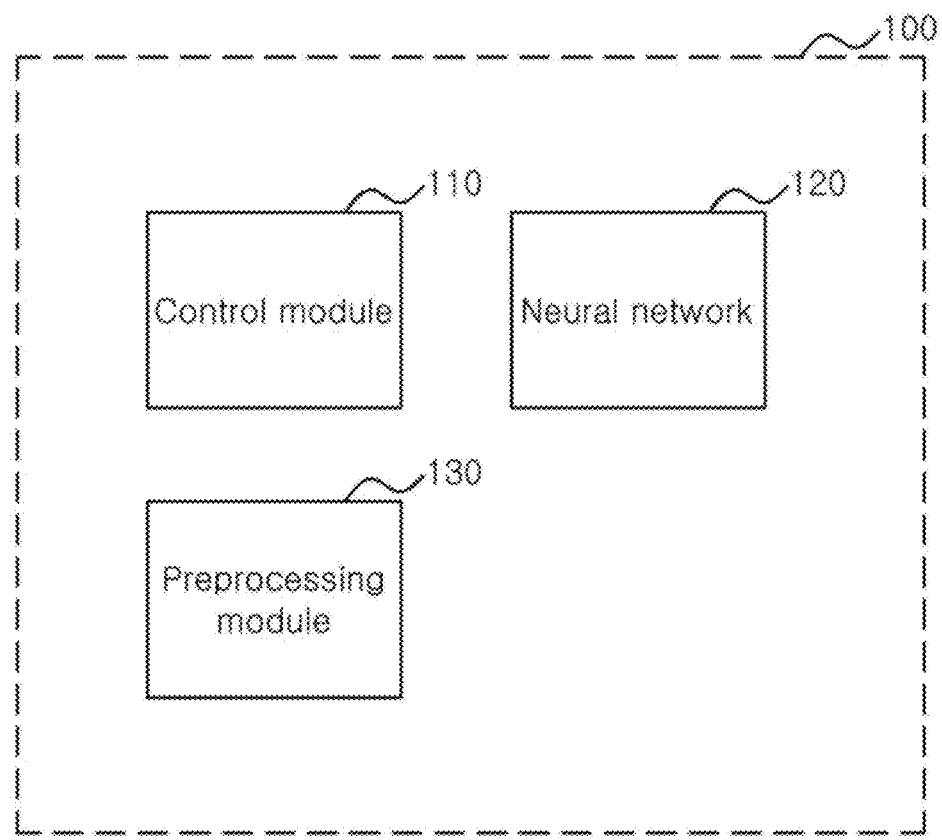
FIG. 2 is a diagram for describing a logical configuration of the disease diagnosis system using a neural network according to an exemplary embodiment.

The diagnosis system 100 for implementing may logically have a configuration such as FIG. 2.

FIG. 2 is a diagram for describing a logical configuration of the disease diagnosis system using a neural network according to the exemplary embodiments.

Referring to FIG. 2, the diagnosis system 100 includes a control module 110 and a neural network module 120 in which the neural network is stored. Furthermore, the diagnosis system 100 may further include a preprocessing module 130.

The diagnosis system 100 may mean a logical configuration including a hardware resource and/or software preferable to implement the exemplary embodiments, and does not essentially mean one physical element one device. That is, the diagnosis system 100 may mean a logical combination of hardware and/or software provided to implement the exemplary embodiments. The diagnosis system 100 may be implemented as a set of logical elements installed on isolated devices, respectively, if preferable, and for implementing the exemplary embodiments by performing respective functions. Furthermore, the diagnosis system 100 may mean a set of elements separately implemented for respective functions or roles for implementing the exemplary embodiments. For example, the control module 110, the neural network module 120 and/or the preprocessing module 130 may be located in different physical devices or may be located in the same physical device. Furthermore, according to an implementation example, a combination of software and/or hardware that constitute the control module 110, the neural network module 120 and/or the preprocessing module 130 may be located in different physical devices, and elements located in a different physical device may be organically combined to implement each of the modules.

Furthermore, in this specification, the module may mean a functional, structural combination of hardware for performing the exemplary embodiments and software for driving the hardware. For example, the module may mean a logical unit of a given code and a hardware resource by which the given code is performed. An average expert in the technical field of the exemplary embodiments may easily infer that the module does not essentially mean a physically connected code or one type of hardware.

The control module 110 may control another element (e.g., the neural network module 120 and/or the preprocessing module 130) included in the diagnosis system 100 in order to implement the exemplary embodiments.

Furthermore, the control module 110 may perform diagnosis according to the exemplary embodiments using the neural network stored in the neural network module 120. When it is said that diagnosis is performed, this may mean that a channel value (feature value) of at least one channel defined in the output layer is output as described above. Each feature value may correspond to the probability that a unitary unit, that is, a target for diagnosis, will correspond to information defined by a corresponding channel.

The neural network module 120 may store the neural network. The neural network may mean a set of information that represents a series of design factors to define the neural network. In this specification, the neural network may be a convolutional neural network. Furthermore, as described above, a known DeepLab neural network may be used as the neural network, and a neural network disclosed in the prior application may be used as the neural network.

In either case, the loss function that enables learning using learning data labeled in a dual class may be defined in the neural network.

As known, the neural network is trained to minimize a loss defined by the loss function.

In this case, according to the exemplary embodiments, if a unitary unit may be labeled in a dual class, that is, if the unitary unit may be labeled as a plurality of states, and in this case, the plurality of states has been labeled to include the first state determined to have a state of a higher probability and the second state determined to have a lower probability than the first state, the loss function may be defined to incorporate, into a loss, both first feature value corresponding to the first state and a second feature value corresponding to the second state, among feature values corresponding to the plurality of states.

The neural network may be defined so that a first feature value corresponding to a corresponding unitary unit has a greater influence than a second feature value.

For example, the entire loss may be defined to be decreased as the first feature value becomes great, the entire loss may be defined to be decreased as the second feature value also become great, and the first feature value may be defined to have a greater influence than the second feature value. Furthermore, feature values corresponding to the remaining states may be defined to have a great loss as the feature value becomes great.

For example, according to the exemplary embodiments, the loss function may be defined to improve conventional cross entropy, that is, to incorporate the second feature value into a loss.

The loss function according to an exemplary embodiment may be the same as Equation 1 below.

$$L(x) = -\log \frac{e^{x_{primary}} + p \cdot e^{x_{secondary}}}{\sum e^{x_i}} \quad \text{[Equation 1]}$$

wherein i indices of a plurality of states, $\chi_i$ is a feature value corresponding to an i-th state among the plurality of states, $\chi_{primary}$ may be the first feature value, and $\chi_{secondary}$ may be the second feature value.

Furthermore, p may have a value between 0 and 1.

For example, the neural network may include a given layer that output feature values corresponding to a plurality of predefined state channels (e.g., the normal, the Gleason score 3, the Gleason score 4, and the Gleason score 5), respectively, when a specific unitary unit is received. The layer may be designed as the final layer, and may be a previous layer of the final layer.

Furthermore, the specific unitary unit may be a unitary unit labeled as a primary state and a secondary state, that is, a dual class.

In such a case, when a feature value of the primary state is great, that is, as a feature value corresponding to the primary state among feature values output by the neural network, becomes great, a value of $e^{\chi_{primary}}$ is increased. As a result, the entire loss may be decreased. Likewise, as a feature value corresponding to the secondary state becomes great, a value of $e^{\chi_{secondary}}$ is increased. As a result, the entire loss may be decreased. However, the feature value of the primary state has a great influence in reducing a loss because p has a value smaller than 1 compared to the feature value of the secondary state.

As feature values corresponding to other states become great, only a value of $e^{\chi_i}$ becomes great. As a result, only a loss is increased.

Accordingly, the neural network may be trained by the aforementioned loss function so that the primary state has a great value, the secondary state has a relatively great value (although the secondary state has a smaller value than the primary state), and the remaining states have small value as much as possible. The results of a dual class actually labeled by an expert may be incorporated into the learning.

Meanwhile, as described above, a criterion for determining the accuracy of the neural network if a unitary unit is labeled to permit the dual class may be as follows.

In a conventional technology, in order to calculate accuracy, the accuracy was calculated using a confusion matrix. The confusion matrix is a matrix in which the number of predicted values "B" whose answer is "A" is indicated at locations (A, B). Pixel unit accuracy and performance of segmentation, such as an intersection over union (IoU), are measured based on the confusion matrix. In a conventional technology, since only a simple answer was present, only a correct or wrong result was present. However, according to the exemplary embodiments, two answers "primary" and "secondary" are present. Accordingly, it is preferable to calculate the confusion matrix in a slightly different manner.

If an answer is given as the primary or another answer other than both the primary and the secondary is given, as in a conventional technology, this is incorporated into the confusion matrix. However, if an answer is given as the secondary, the answer is wrong for a primary answer, but may be considered as being correct for a secondary answer. Accordingly, the confusion matrix may be calculated by applying p to (the primary, the secondary) and p−1 to (the secondary, the secondary). In this case, p may be a value determined between 0 and 1.

Meanwhile, the control module 110 may receive input data to the neural network stored in the neural network module 120, that is, the trained neural network. Furthermore, output data may be output by performing operations defined by the neural network.

The preprocessing module 130 may perform preprocessing on a required biometric image before performing diagnosis using the neural network. For example, the preprocessing of the biometric image may include a process of the biometric image into unitary units having a predefined size. If preferable, the unitary unit may be a pixel unit, and the preprocessing module 130 may not be preferable. In addition to such segmentation into unitary units, an average expert in the technical field of the exemplary embodiments may easily infer that the preprocessing of the biometric image may be performed by various preprocessing modules 130 for training the neural network, if preferable.

As described above, the neural network may include a layer that outputs predetermined states (e.g., the normal, the Gleason score 3, the Gleason score 4, and the Gleason score 5) of a corresponding input unitary unit as feature values, respectively, with respect to a given disease.

Figure 4:
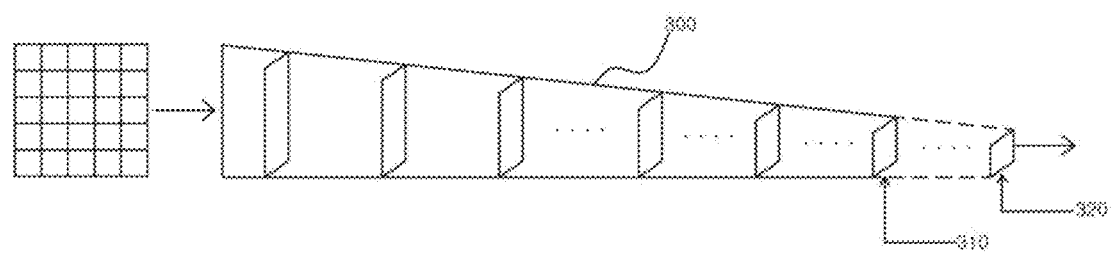
FIG. 4 is a diagram for conceptually describing a configuration of a neural network according to another exemplary embodiment.

An example in which such a neural network is conceptually illustrated may be the same as FIG. 4.

FIG. 4 is a diagram for conceptually describing a configuration of the neural network according to another exemplary embodiment.

Referring to FIG. 4, the neural network 300 according to exemplary embodiments may receive a given unitary unit (e.g., a pixel or a patch) as illustrated in FIG. 4. FIG. 4 illustrates a case where a patch obtained by segmenting a biometric image in a given size (e.g., 512 by 512) is input, but a pixel value (e.g., RGB 3-channel value) may be input as input data in each patch unit.

If the unitary unit is pixel, a given experienced expert may mark a specific region in a biometric image using a given tool, and may perform labeling on the marked region. A pixel included in the labeled region may have a labeling value in the corresponding region.

If the unitary unit is a patch, labeling may be performed on each patch.

As described above, the neural network 300 may be a known DeepLab model and may be the neural network disclosed in the prior application. Alternatively, the neutral network 300 may be another neural network.

In either case, the neural network 300 may include a given layer (e.g., 310). The layer (e.g., 310) may be a layer that outputs feature values of the unitary unit corresponding to a plurality of states. For example, the layer may output feature values corresponding to four channels, respectively. The feature values may be values corresponding to probabilities corresponding to a plurality of predetermined states (e.g., the normal, the Gleason score 3, the Gleason score 4, and the Gleason score 5).

The layer (e.g., 310) may be the final layer. The final layer (e.g., 320) may be further present right after the layer 310. In such a case, the final layer (e.g., 320) may be a layer that outputs a state having the greatest value among feature values of the layer (e.g., 310).

In either case, the output value output by the layer (e.g., 310) may be a result trained to minimize a loss by the loss function defined in the neural network 300.

As described above, the loss function may be defined to reduce the entire loss with respect to a specific unitary unit labeled in a dual class as a feature value of the primary state becomes great, a feature value of the secondary state also becomes great although the value is smaller than that of the primary state, and feature values of the remaining states become small.

Such an example may be Equation 1, but is not limited thereto. The loss function may include another exemplary embodiment.

Accordingly, an actually confusable unitary unit may have its confusable state itself incorporated into learning, thus generally improving performance.

A case where the type of disease diagnosed by the diagnosis system 100 is prostate cancer is described as an example, but an average expert in the technical field of the exemplary embodiments may easily infer that the exemplary embodiments does not need to be essentially limited and applied to prostate cancer.

Meanwhile, if the unitary unit is a pixel, when each pixel has a preset determination value (e.g., the Gleason score 3 to 5), the diagnosis system 100 may determine a corresponding pixel as a disease pixel corresponding to a disease based on a determined value of a pixel unit. Furthermore, the diagnosis system 100 may indicate the disease pixel differently from anther pixel in the biometric image based on the determination result.

That is, according to the exemplary embodiments, diagnosis may be performed in a pixel unit. In such a case, a portion in which a disease has been revealed in the biometric image may be segmented.

Figure 5A:
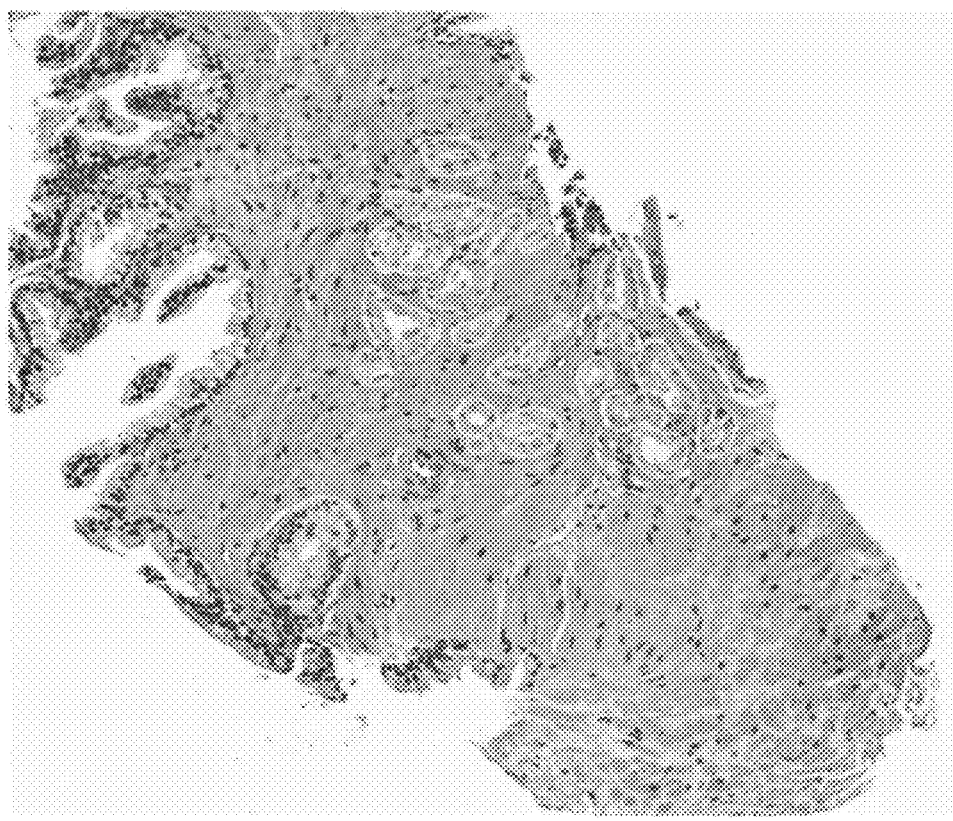
FIGS. 5A and 5B are diagrams illustrating simulation results according to an exemplary embodiment.
Figure 5B:
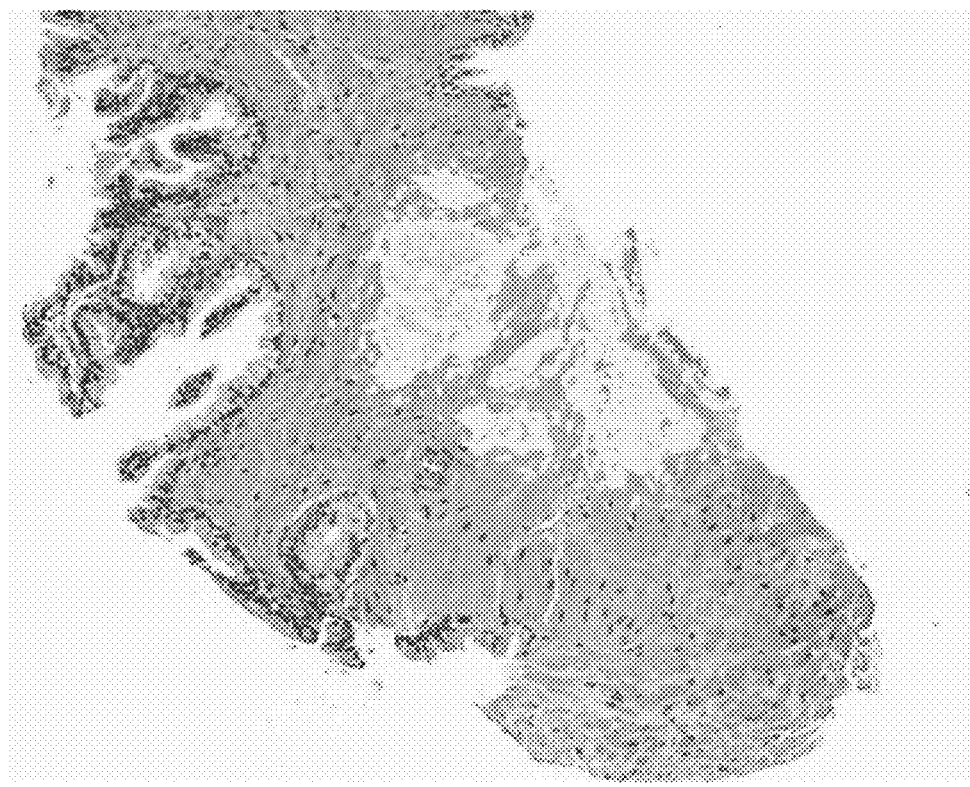

Such an example may be the same as that illustrated in FIGS. 5A and 5B.

FIGS. 5A and 5B are diagrams illustrating simulation results according to the exemplary embodiments.

A left portion as depicted by FIG. 5A may indicate a biometric image labeled by an experienced expert, and each labeled region may indicate a region in which a disease has been revealed.

Furthermore, a right portion as depicted by FIG. 5B is a diagram illustrating results in which a pixel determined to have a disease revealed in a pixel unit according to the exemplary embodiments was represented (e.g., indicated in yellow) differently from another portion and segmentation was performed in a pixel unit.

Through such segmentation, there is an effect in that finer segmentation can be performed compared to conventional results in which diagnosis and segmentation are performed in a patch unit.

Furthermore, in this specification, an example in which the exemplary embodiment has been applied to prostate cancer has been chiefly described. However, an average expert in the technical field of the exemplary embodiments may easily infer that accurate diagnosis can be performed if the exemplary embodiments is applied to another disease whose state can be divided into a plurality of states.

The disease diagnosis method supporting a dual class according to the exemplary embodiments may be implemented in a computer-readable recording medium in the form of computer-readable code. The computer-readable recording medium includes all types of recording devices in which data readable by a computer system is stored. Examples of the computer-readable recording medium may include a ROM, a RAM, a CD-ROM, magnetic tapes, floppy disks, and optical data storages. Furthermore, the computer-readable recording medium may be distributed to computer systems connected over a network, and may have a computer-readable code stored and executed in a distributed manner. Furthermore, a functional program, a code and code segments for implementing the exemplary embodiments may be easily reasoned by programmers of the technical field to which the exemplary embodiments pertains.

The exemplary embodiments may be used in a "disease diagnosis system supporting a dual class and a method thereof."

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A disease diagnosis system comprising:
a processor and a storage device storing a neural network having at least an initial layer, a final layer, and a layer preceding the final layer that is different from the initial layer, and using a biometric image and the neural network, wherein:
the processor is configured to train the neural network and store the neural network in the storage device to output a determination value corresponding to a probability having at least one of a plurality of states using a given loss function and learning data labeled so that a given unitary unit included in the biometric image that includes a plurality of unitary units is to have at least one of the plurality of states,
the neural network comprises the initial layer, the final layer, and the layer preceding the final layer to output, by the final layer, a plurality of feature values corresponding to a probability that the unitary unit is to be determined as each of the plurality of states, and
the loss function is defined to calculate a loss by incorporating both a first feature value corresponding to a first state and a second feature value corresponding to a second state, among feature values of the initial layer, the final layer, and the layer preceding the final layer, into a dual labeling unitary unit labeled to have the plurality of states, comprising the first state determined to have a state of a higher probability and a second state determined to be lower than the first state, among multiple unitary units included in the biometric image,
wherein the loss function is defined so that the second feature value has more losses than the first feature value, and
wherein the loss function is defined as Equation 1 below, $$L(x) = -\log \frac{e^{x_{primary}} + p \cdot e^{x_{secondary}}}{\sum e^{x_i}}, \quad \text{[Equation 1]}$$

wherein i indices the plurality of states, $x_i$ is a feature value corresponding to an i-th state among the plurality of states, $x_{primary}$ is the first feature value, and $x_{secondary}$ is the second feature value.

2. The disease diagnosis system of claim 1, wherein the unitary unit is a pixel unit of the biometric image.

3. The disease diagnosis system of claim 2, wherein if each pixel has a preset determination value, the processor determines a corresponding pixel as a disease pixel corresponding to a disease based on a determination value of the pixel unit and indicates the disease pixel differently from another pixel in the biometric image based on a result of the determination.

4. The disease diagnosis system of claim 1, wherein the disease is prostate cancer.

5. The disease diagnosis system of claim 4, wherein the plurality of states comprises a normal, a Gleason score 3, a Gleason score 4, and a Gleason score 5.

6. A method implemented in a system comprising a processor and a storage device and performed by a disease diagnosis system using a biometric image and a neural network having at least an initial layer, a final layer, and a layer preceding the final layer that is different from the initial layer, the method comprising steps of:

receiving, by the neural network stored in the storage device, a given loss function and learning data labeled so that a given unitary unit included in the biometric image that includes a plurality of unitary units is to have at least one of a plurality of states;

training to output a determination value corresponding to a probability having at least one of the plurality of states using the received learning data with respect to each unitary unit, the neural network comprises the initial layer, the final layer, and the layer preceding the final layer to output, by the final layer, a plurality of feature values corresponding to a probability that the unitary unit is to be determined as each of the plurality of states, and the loss function is defined to calculate a loss by incorporating both a first feature value corresponding to a first state and a second feature value corresponding to a second state, among feature values of the the initial layer, the final layer, and the layer preceding the final layer, into a dual labeling unitary unit labeled to have the plurality of states, comprising the first state determined to have a state of a higher probability and a second state determined to be lower than the first state, among multiple unitary units included in the biometric image, wherein the loss function is defined so that the second feature value has more losses than the first feature value, wherein the loss function is defined as Equation 1 below, $$L(x) = -\log \frac{e^{x_{primary}} + p \cdot e^{x_{secondary}}}{\sum e^{x_i}},$$ [Equation 1]

wherein i indices the plurality of states, $\chi_i$ is a feature value corresponding to an i-th state among the plurality of states, $\chi_{primary}$ is the first feature value, and $\chi_{secondary}$ is the second feature value.

7. The method of claim 6, further comprising steps of:

determining a corresponding pixel as a disease pixel corresponding to a disease based on a determination value of the pixel unit if each pixel has a preset determination value, and indicating the disease pixel differently from another pixel in the biometric image based on a result of the determination.

8. A non-transitory computer readable medium storing a computer program installed in a data processor and written in the non-transitory computer readable medium for performing the method according to claim 6.

* * * * *